United States Patent
Mande et al.

(10) Patent No.: US 11,996,170 B2
(45) Date of Patent: May 28, 2024

(54) METHOD AND SYSTEM FOR IDENTIFICATION AND CLASSIFICATION OF OPERATIONAL TAXONOMIC UNITS IN A METAGENOMIC SAMPLE

(71) Applicant: Tata Consultancy Services Limited, Mumbai (IN)

(72) Inventors: Sharmila Shekhar Mande, Pune (IN); Deepak Yadav, Pune (IN); Anirban Dutta, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 928 days.

(21) Appl. No.: 16/045,439

(22) Filed: Jul. 25, 2018

(65) Prior Publication Data
US 2019/0034588 A1  Jan. 31, 2019

(30) Foreign Application Priority Data
Jul. 28, 2017 (IN) .............................. 201721027000

(51) Int. Cl.
| | | |
|---|---|---|
| *C12Q 1/689* | (2018.01) | |
| *C12Q 1/6809* | (2018.01) | |
| *C12Q 1/6869* | (2018.01) | |
| *G16B 10/00* | (2019.01) | |
| *G16B 20/00* | (2019.01) | |
| *G16B 30/00* | (2019.01) | |
| *G16B 40/00* | (2019.01) | |
| *G16B 40/10* | (2019.01) | |
| *G16B 50/00* | (2019.01) | |
| *G16B 50/10* | (2019.01) | |

(52) U.S. Cl.
CPC ........... *G16B 50/10* (2019.02); *C12Q 1/6809* (2013.01); *C12Q 1/6869* (2013.01); *C12Q 1/689* (2013.01); *G16B 10/00* (2019.02); *G16B 20/00* (2019.02); *G16B 30/00* (2019.02); *G16B 40/00* (2019.02); *G16B 50/00* (2019.02); *C12Q 2600/158* (2013.01); *G16B 40/10* (2019.02)

(58) Field of Classification Search
None
See application file for complete search history.

(56) References Cited

U.S. PATENT DOCUMENTS

2016/0228003 A1  8/2016  Apte et al.

OTHER PUBLICATIONS

Matsen, Phylogenetics and the Human Microbiome Syst. Biol. 64(1):e26-e41, 2015, Advance Access publication Aug. 7, 2014, DOI:10.1093/sysbio/syu053.*

X. Hao, et al. "OUT Analysis Using Metagenomic Shotgun Sequencing Data," retrieved from https://doi.org/10.1371/journal.pone.0049785 on Jul. 24, 2018, dated Nov. 26, 2006 (11 pages).

* cited by examiner

*Primary Examiner* — Joseph Woitach
(74) *Attorney, Agent, or Firm* — FINNEGAN, HENDERSON, FARABOW, GARRETT & DUNNER LLP

(57) ABSTRACT

A system and method for identification and classification of operational taxonomic units (OTUs) in a metagenomic sample using short read amplicon sequences has been described. The disclosure enables accurate identification of OTU in a metagenomic sample and provides a framework for easy cross comparison of microbiome community structures sampled across different disconnected metagenomic studies. Instead of using a reference database consisting of full-length marker genes directly for taxonomic classification or OTU-picking, the present disclosure creates customized OTU databases for different hyper-variable regions of a marker gene. These databases consist of reference OTUs obtained through independent clustering of sequences pertaining to different selected hyper-variable regions of the marker gene. In another embodiment, mapping back is also provided facilitating cross comparison between results obtained from different studies that may have utilized different hyper-variable regions. The system results in enhanced accuracy of classification of operational taxonomic units (OTUs) in the metagenomic sample.

7 Claims, 4 Drawing Sheets

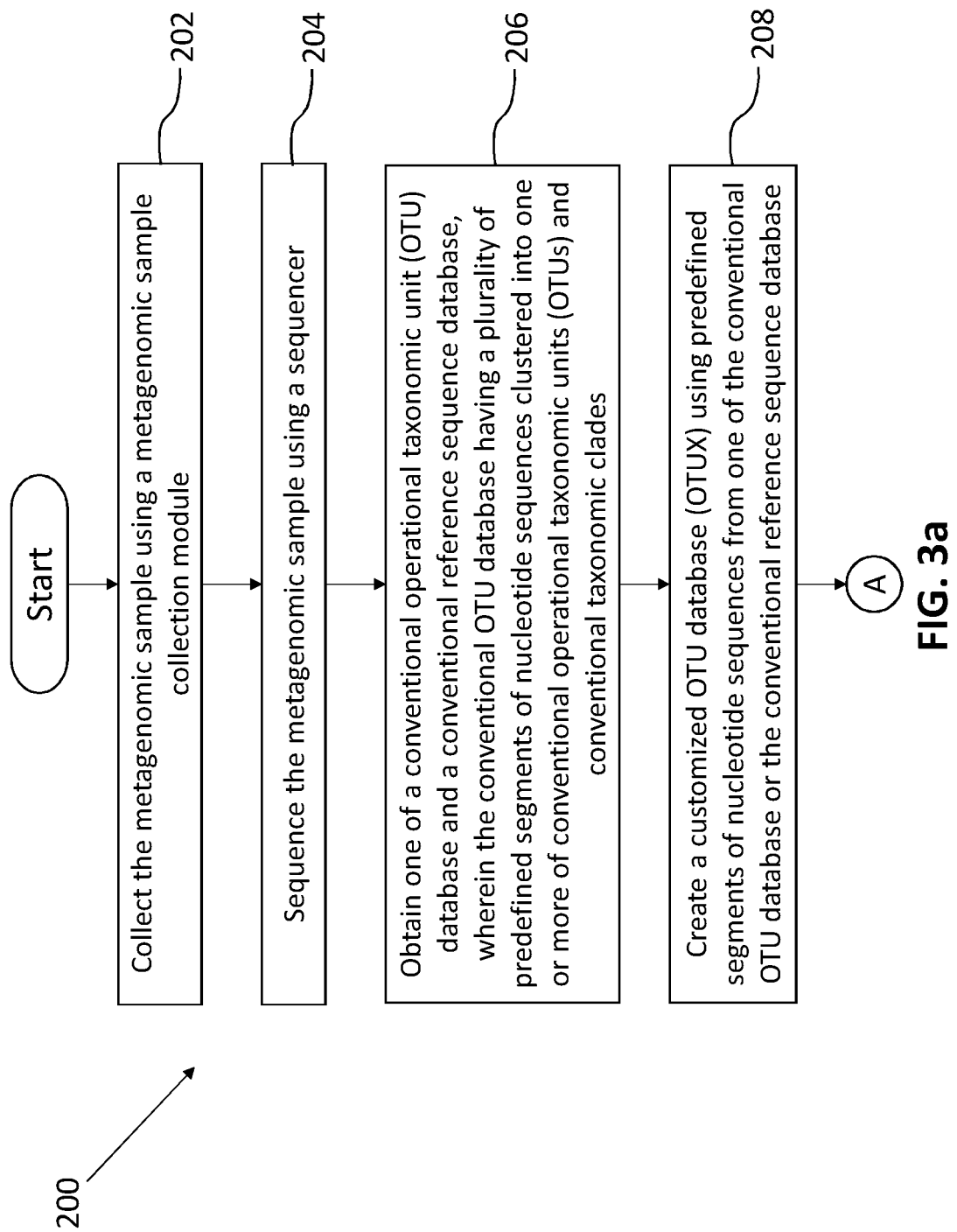

METHOD AND SYSTEM FOR IDENTIFICATION AND CLASSIFICATION OF OPERATIONAL TAXONOMIC UNITS IN A METAGENOMIC SAMPLE

PRIORITY CLAIM

This U.S. patent application claims priority under 35 U.S.C. § 119 to: India Application No. 201721027000, filed on 28 Jul. 2017. The entire contents of the aforementioned application are incorporated herein by reference.

TECHNICAL FIELD

The embodiments herein generally relates to the field of improving taxonomic classification accuracies of metagenomic sample, and, more particularly, to a method and system for identification and classification of operational taxonomic units in a metagenomic sample using short read amplicon sequences.

BACKGROUND

Metagenomic studies employ DNA sequencing of phylogenetic marker genes to ascertain the microbial community structure pertaining to a sampled environment and for taxonomic classification of the inhabiting microbial organisms. However, the current generation of cost effective high-throughput DNA sequencing technologies, can only generate short 'reads' (DNA sequence fragments of ~300-600 base pairs in length) which is not sufficient to cover the entire length of phylogenetic marker genes. For example, the most common phylogenetic marker used for bacterial taxonomic classification is the 16S rRNA gene which is around 1500 bp long. Given that only a short region from this gene can be targeted for DNA sequencing using current generation sequencing technologies, experiments are designed to utilize specific 'hyper-variable regions' (V regions) in the 16S rRNA gene.

During the taxonomic classification step, these short sequences are compared against existing 16S rRNA gene catalogues (through sequence similarity searches) to identify the strain, species, genus, etc., to which their origin may be attributed. Alternately, all sequences belonging to a sample/environment are clustered based on sequence similarity, wherein sequences which have been clustered together (having significant sequence similarity) may be considered to have originated from the same group of organisms, also known as an operational taxonomic unit (OTU).

The present methods in the prior art includes reference database based classification and de novo OTU picking. The reference database based classification method works well for a sampled environment whose resident microbes have already been catalogued through previous studies. The de novo OTU picking method enables identification/detection of taxonomic groups present in the sampled environment even though they have not been characterized/taxonomically-classified earlier. Both the methods have few drawbacks.

The current methods for reference database based OTU identification or taxonomic classification rely on databases cataloguing full-length marker genes (e.g. 16S rRNA genes) or reference OTUs identified through clustering full-length marker genes. Since the query reads/sequences used during the comparison are only 'short-reads', the OTU identification/classification results can be inaccurate and sub-optimal.

Further, rate of evolution (accumulation of mutations) is not always uniform across the length of a chosen marker gene in different taxonomic clades. It is possible that a short region remains identical during the course of evolution, whereas flanking regions are more prone to mutations. Alternately, a major fraction of the marker gene may remain unchanged through evolution barring a small hyper-variable stretch. Given this, OTU clustering results can significantly vary based on the short region chosen for sequencing. OTUs identified/classified using reference based vs de novo methods will provide different results given the above reasons.

SUMMARY

Embodiments of the present disclosure present technological improvements as solutions to one or more of the above-mentioned technical problems recognized by the inventors in conventional systems. For example, in one embodiment, a system is provided for identification and classification of operational taxonomic units (OTUs) in a metagenomic sample using short read amplicon sequences. The system comprises a conventional OTU database and a conventional reference sequence database, metagenomic sample collection module, a sequencer, a memory and a processor. The conventional OTU database and the conventional reference sequence database having a plurality of nucleotide sequences clustered into one or more of conventional operational taxonomic units (OTUs) and conventional taxonomic clades. The metagenomic sample collection module collects the metagenomic sample a memory. The sequencer sequences the collected metagenomic sample. The processor configured to perform the steps of: creating a customized OTU database (OTUX) out of the sequenced metagenomic sample using a plurality of predefined segments of nucleotide sequences from one of the conventional OTU database or the conventional reference sequence database, wherein the predefined segments of nucleotide sequences are clustered into customized OTUs using a sequence clustering technique; calculating propensity of a customized OTU from the customized OTU database (OTUX) using a predefined formula, wherein the propensity refers to a probability of a customized OTU being associated with one or more conventional taxonomic clades in the conventional reference sequence database and the conventional OTUs in the conventional OTU database; creating a mapping matrix listing all values of propensities for each of the customized OTUs with respect to one or more conventional taxonomic clades and conventional OTUs; utilizing the customized OTU database (OTUX) as a reference database for open reference OTU picking to classify the short read amplicon sequences corresponding to predefined segments in to appropriate customized OTUs; and building an abundance table depicting the proportion of the short read amplicon sequences classified into each of the customized OTUs, wherein the abundance table representing enhanced accuracy of classification of operational taxonomic units (OTUs) in the metagenomic sample.

In another embodiment, a method is provided for identification and classification of operational taxonomic units (OTUs) in a metagenomic sample using short read amplicon sequences. Initially, the metagenomic sample is collected using a metagenomic sample collection module. The metagenomic sample is then sequenced using a sequencer. In the next step, one of a conventional operational taxonomic unit (OTU) database and a conventional reference sequence database is obtained, wherein the conventional OTU database having a plurality of nucleotide sequences clustered into one or more of conventional operational taxonomic units (OTUs) and conventional taxonomic clades. In the next step, a customized OTU database (OTUX) is created out of the sequenced metagenomic sample using a plurality of predefined segments of nucleotide sequences from one of the conventional OTU database or the conventional reference sequence database, wherein the predefined segments of nucleotide sequences are clustered into customized OTUs using a sequence clustering technique. In the next step, the propensity of a customized OTU from the customized OTU database (OTUX) is calculated using a predefined formula, wherein the propensity refers to a probability of a customized OTU being associated with one or more conventional taxonomic clades in the conventional reference sequence database and the conventional OTUs in the conventional OTU database. A mapping matrix is then created listing all values of propensities for each of the customized OTUs with respect to one or more conventional taxonomic clades and conventional OTUs. In the next step, the customized OTU database (OTUX) is utilized as a reference database for open reference OTU picking to classify the short read amplicon sequences corresponding to predefined segments in to appropriate customized OTU. And finally, an abundance table is built depicting the proportion of the short read amplicon sequences classified into each of the customized OTUs, wherein the abundance table representing enhanced accuracy of classification of operational taxonomic units (OTUs) in the metagenomic sample.

In yet another embodiment, a non-transitory computer-readable medium having embodied thereon a computer program is provided for identification and classification of operational taxonomic units (OTUs) in a metagenomic sample using short read amplicon sequences. Initially, the metagenomic sample is collected using a metagenomic sample collection module. The metagenomic sample is then sequenced using a sequencer. In the next step, one of a conventional operational taxonomic unit (OTU) database and a conventional reference sequence database is obtained, wherein the conventional OTU database having a plurality of nucleotide sequences clustered into one or more of conventional operational taxonomic units (OTUs) and conventional taxonomic clades. In the next step, a customized OTU database (OTUX) is created out of the sequenced metagenomic sample using a plurality of predefined segments of nucleotide sequences from one of the conventional OTU database or the conventional reference sequence database, wherein the predefined segments of nucleotide sequences are clustered into customized OTUs using a sequence clustering technique. In the next step, the propensity of a customized OTU from the customized OTU database (OTUX) is calculated using a predefined formula, wherein the propensity refers to a probability of a customized OTU being associated with one or more conventional taxonomic clades in the conventional reference sequence database and the conventional OTUs in the conventional OTU database. A mapping matrix is then created listing all values of propensities for each of the customized OTUs with respect to one or more conventional taxonomic clades and conventional OTUs. In the next step, the customized OTU database (OTUX) is utilized as a reference database for open reference OTU picking to classify the short read amplicon sequences corresponding to predefined segments in to appropriate customized OTU. And finally, an abundance table is built depicting the proportion of the short read amplicon sequences classified into each of the customized OTUs, wherein the abundance table representing enhanced accuracy of classification of operational taxonomic units (OTUs) in the metagenomic sample.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 3a-3b is a flowchart illustrating the steps involved in identification and classification of operational taxonomic units (OTUs) in a metagenomic sample using short read amplicon sequences according to an embodiment of the present disclosure.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Glossary—Terms Used in the Embodiments

The expression "operational taxonomic units" or "OTUs" in the context of the present disclosure refers to sequences which have been clustered together (having significant sequence similarity) and may be considered to have originated from the same group of organisms. Generally operational taxonomic units are defined based on the similarity threshold. While a customized OTU database will be referred as "OTUX"

Figure 1:
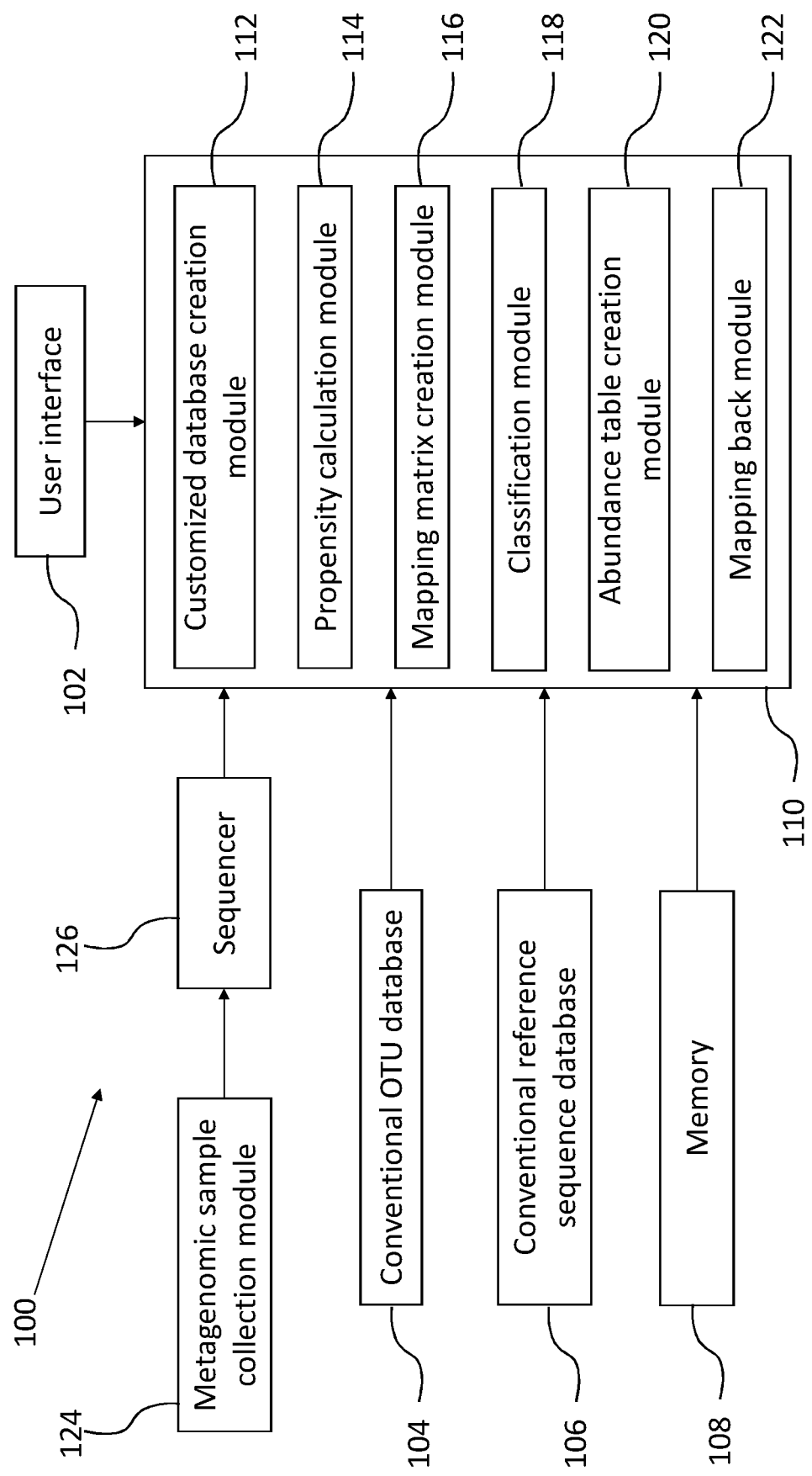
FIG. 1 illustrates a block diagram for identification and classification of operational taxonomic units (OTUs) in a metagenomic sample using short read amplicon sequences according to an embodiment of the present disclosure.
Figure 2:
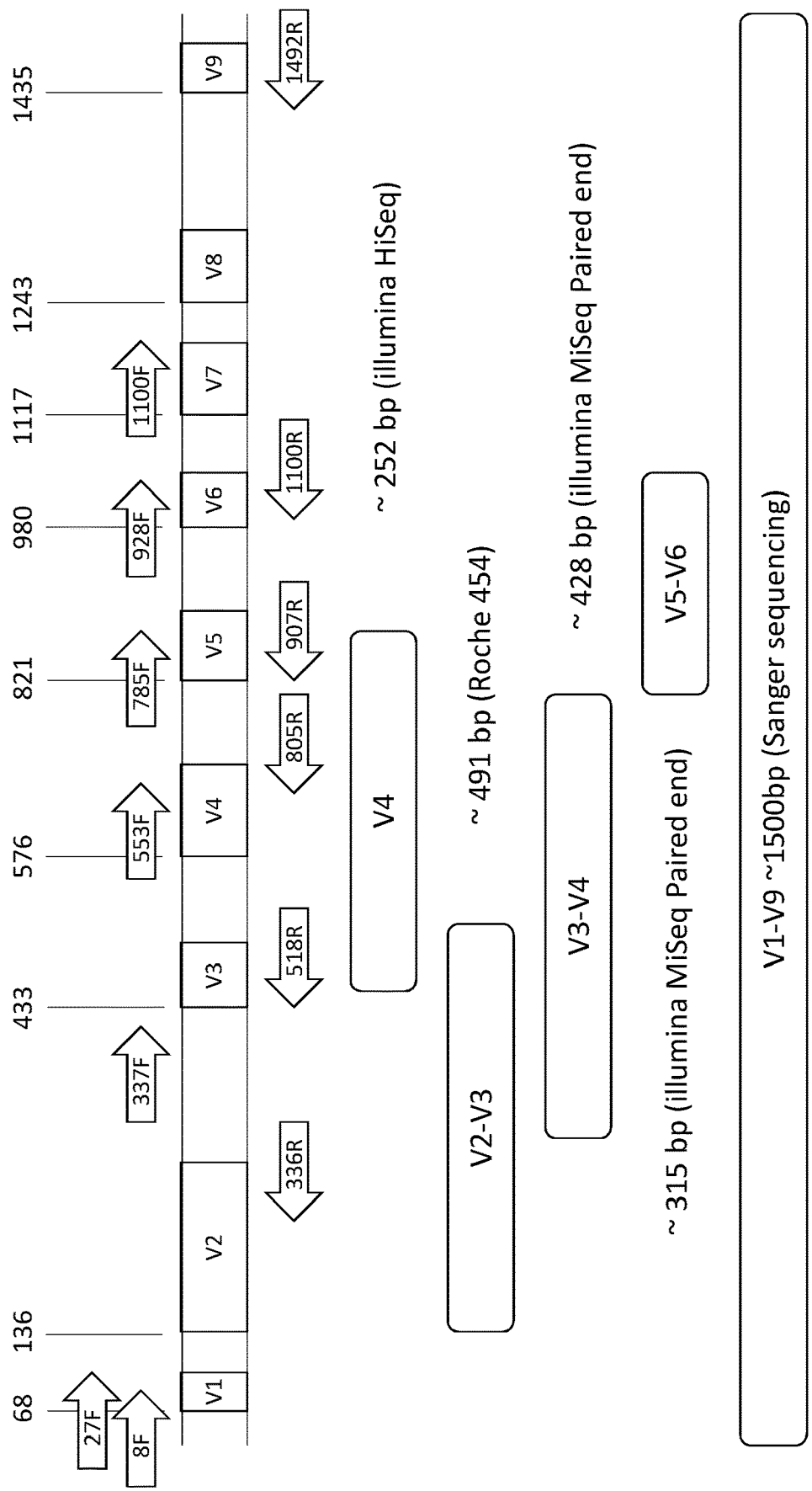
FIG. 2 shows organization of the different hyper-variable regions on 16S rRNA gene according to an embodiment of the disclosure.
Figure 3B:
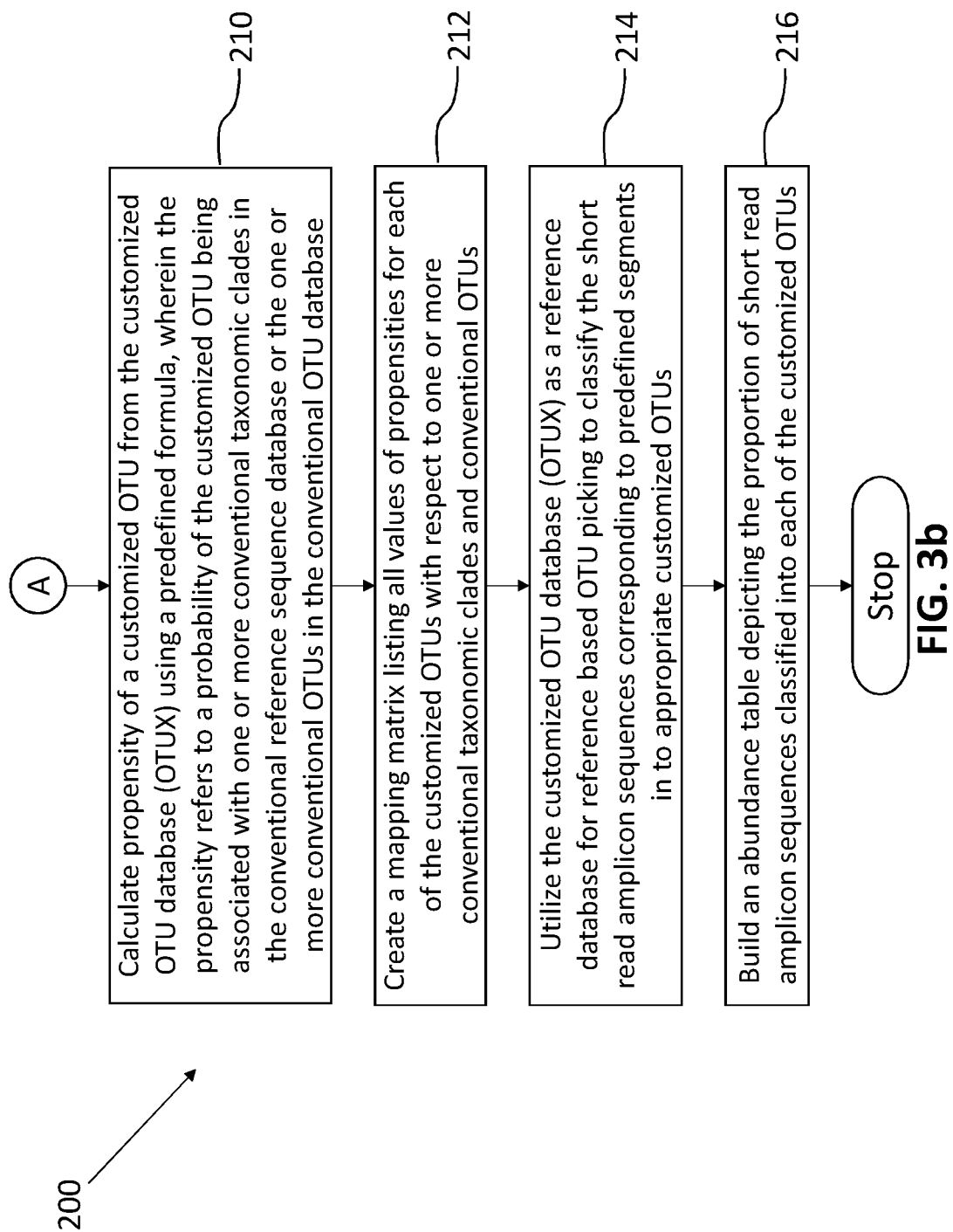

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

According to an embodiment of the disclosure, a system 100 for identification and classification of operational taxonomic units (OTUs) in a metagenomic sample using short read amplicon sequences is shown in FIG. 1. The disclosure pertains to a method and a system of improving taxonomic classification accuracies of metagenomic sequences obtained through short read amplicon sequencing. The disclosure also provides a framework for easy cross comparison of microbiome community structures sampled across different disconnected metagenomic studies, wherein different sequencing technologies as well as different marker sequences or amplicons may have been used.

According to an embodiment of the disclosure, the system 100 consists of a user interface 102, a conventional OTU database 104, a conventional reference sequence database 106, a memory 108 and a processor 110 as shown in FIG. 1. The processor 110 is in communication with the memory 108. The processor 110 configured to execute a plurality of algorithms stored in the memory 108. The processor 110 further includes a plurality of modules for performing various functions. The processor 110 may include customized database creation module 112, a propensity calculation module 114, a mapping matrix creation module 116, a classification module 118, an abundance table creation module 120 and a mapping back module 122.

According to an embodiment of the disclosure, the system 100 further includes a metagenomic sample collection module 124 and a sequencer 126. The metagenomic sample is collected from the gut of an individual using the metagenomic sample collection module 124. Though it should be appreciated that the metagenomic sample can also be collected from any other environments such as skin, sea, soil, etc. DNA fragments, extracted from the metagenomic sample are then sequenced using a sequencer 126. The sequenced DNA is then provided to the processor 110 using the user interface 102. The sequenced DNA samples are also referred as 'query' sequences. The user interface 102 is operated by a user. The user interface 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

According to an embodiment of the disclosure, the system 100 includes two pre-computed databases, i.e. the conventional OTU database 104 and the conventional reference sequence database 106. The conventional OTU database 104 and the conventional reference sequence database 106 have a plurality of nucleotide sequences clustered into one or more of conventional operational taxonomic units (OTUs), and one or more conventional taxonomic clades respectively. It should be appreciated that the two pre-computed database are available in the prior art. Use of any other database is well within the scope of this disclosure.

According to an embodiment of the disclosure, the workflow has two major components, viz. (1) a onetime preprocessing to create a customized OTU database called OTUX reference databases and a 'mapping matrix' (MAPMAT) for different V-regions and (2) an open-reference OTU-picking cum taxonomic assignment/classification step using the OTUX reference database(s). The open reference OTU picking involves OTU picking and taxonomic classification of short read metagenomic sequences targeting the V4 region. Followed by open-reference OTU-picking approach, initially a reference based OTU assignment is performed on the query set of metagenomic sequences using the OTUXV4 as the reference database, wherein each of the query sequences are classified into appropriate OTUXV4 OTUs subject to a confidence threshold.

The system 100 includes the customized database creation module 112 to create the customized OTU database (OTUX). The customized OTU database (OTUX) comprises a plurality of customized OTUs. The customized OTU database (OTUX) is created using predefined segments of nucleotide sequences from one of the conventional OTU database 104 or the conventional reference sequence database 106. The predefined segment corresponds to a small portion of the full length DNA sequence that can be targeted through amplicon sequencing. Furthermore, different predefined sequences correspond to different portions of the full DNA sequence that can be extracted/amplified using different primers.

According to an embodiment of the disclosure, the system 100 further includes a propensity calculation module 114. The propensity calculation module 114 is configured to calculate the propensity of a customized OTU from the customized OTU database (OTUX) using a predefined formula. The predefined formula is Predefined formula=(number of predefined segments of sequences clustered into a customized OTU corresponding to the customized OTU database (OTUX) whose full-length counterparts are assigned to a conventional OTU or a conventional taxonomic clade present in a conventional OTU database)/(total number of predefined segments of sequences clustered into the customized OTU corresponding to the customized OTU database(OTUX)).

The calculated propensity refers to a probability of a customized OTU being associated with one or more conventional taxonomic clades in the conventional reference sequence database 106 and the one or more conventional OTUs in the conventional OTU database 104. Further the system 100 is configured to create a mapping matrix using the mapping matrix creation module 116. The mapping matrix lists all values of propensities for each of the customized OTUs present in the customized OTU database (OTUX) with respect to one or more conventional taxonomic clades and conventional OTUs.

According to an embodiment of the disclosure, the system 100 further includes the classification module 118. The classification module 118 is configured to utilize the customized OTU database (OTUX) as a reference database for open reference OTU picking to classify the short read amplicon sequences (query sequences) corresponding to the predefined segments in to appropriate customized OTUs. The system 100 is further configured to create an abundance table depicting the proportion of the short read amplicon sequences (query sequences) classified into each of the customized OTUs using the abundance table creation module 120.

According to an embodiment of the disclosure, the system 100 can be extended for OTU picking and taxonomic classification of metagenomes using any marker genes/regions of nucleotide sequences obtained from the metagenomic sample. However, for illustrative purpose, the present disclosure exemplifies the method and applicability using the following: Marker gene—prokaryotic 16S rRNA gene (having 9 hyper-variable regions V1-V9); Hyper-variable region—V4 (hyper-variable region 4); Conventional reference OTU database—Greengenes 13.8 (containing full length 16S rRNA sequences grouped into conventional OTUs). FIG. 2 shows organization of the different hyper-variable regions on 16S rRNA gene according to an embodiment of the disclosure. According to another embodiment of the disclosure, the marker gene can be any other gene along with their hyper-variable regions, for example, ITS, 23S rRNA, 18S rRNA gene etc.

Initially, all 'prokMSA' unaligned sequences from Greengenes database (v13.8 used in this embodiment) are retrieved. For each of these sequences, taxonomic classification for different taxonomic hierarchical levels including phylum, class, order, family, genus, species as well as corresponding Greengenes OTU IDs (conventional OTU IDs) are also retrieved. In the next step, the V4 region is extracted from each sequence present in the database. The extracted sequences are then clustered based on sequence similarity, wherein each resultant cluster constitutes sequences which share 99% sequence identity with each other. Cd-hit was used for clustering sequences in this embodiment, with reference is taken from the research paper: "Cd-hit: a fast program for clustering and comparing large sets of protein or nucleotide sequences" by Weizhong Li & Adam Godzik Bioinformatics, (2006) 22:1658-9. In the next step, each cluster (OTU) is assigned a unique 'OTUXV4 ID' (say OTUXV4i), and all clusters are compiled to constitute an 'OTUXV4 reference database'. In the next step, a propensity (MAPMATV4i,j) of OTUXV4i being associated to a Greengenes OTU (GGj) is calculated using the following formula:

MAPMATV4i,j=(number of sequences clustered into OTUXV4i whose full-length counterparts are assigned to GGj)/(total number of sequences clustered into OTUXV4i)

Further, the MAPMATV4 propensity matrix is populated for the OTUXV4 database by computing all values for MAPMATV4i,j where,
i=1 to total number of OTUXV4 OTUs (say NOTUX),
j=1 to total number of Greengenes OTUs (say NGG),
and MAPMATV4 is a NGG×NOTUX matrix.

$$MAPMAT_{V4} = \begin{pmatrix} MAPMATv4\ 1,1 & MAPMATv4\ 2,1 & MAPMATv4\ 3,1 & \ldots & MAPMATv4\ i,1 \\ MAPMATv4\ 1,2 & MAPMATv4\ 2,2 & MAPMATv4\ 3,2 & \ldots & MAPMATv4\ i,2 \\ MAPMATv4\ 1,3 & MAPMATv4\ 2,3 & MAPMATv4\ 3,3 & \ldots & MAPMATv4\ i,3 \\ \vdots & \vdots & \vdots & \ldots & \vdots \\ MAPMATv4\ 1,j & MAPMATv4\ 2,j & MAPMATv4\ 3,j & \ldots & MAPMATv4\ i,j \end{pmatrix}$$

In the next step, OTU picking and taxonomic classification of short read metagenomic sequences targeting the V4 region is performed. Following open-reference OTU-picking approach, initially a reference based OTU assignment is performed on the query set of metagenomic sequences using the OTUXV4 as the reference database, wherein each of the query sequences are classified into appropriate OTUXV4 OTUs subject to a confidence threshold. The classification algorithm used may be the naïve Bayesian classifier as used by RDP (Wang's algorithm) with a bootstrap confidence threshold of 80%, in one embodiment. In the next step, the sequences which cannot be classified into existing OTUXV4 OTUs, are further clustered (e.g. using CD-HIT with 99% sequence identity threshold) into 'denovo OTUs'. In the next step, an OTU abundance table (TOTUX) is generated by cumulating the total number of sequenced reads from a metagenomic sample that could be classified/attributed to each of the OTUXV4 OTUs. The classification results obtained in terms of OTUXV4 OTUs are mapped back using MAPMATV4 to represent the results in terms of conventionally used full-length 16S rRNA sequence database (Greengenes v13.8 in this embodiment) OTU IDs.

According to an embodiment of the disclosure, the mapping back can be achieved using two alternate methods. In the first method, to assign each of the query sequences to a particular Greengenes OTU ID, the following process is followed:

For a particular query sequence 's' which has been assigned to the OTU OTUXV4x, the MAPMATV4 elements {MAPMATV4x,j} are retrieved (wherein 'j'=1→NGG i.e. the total no. of Greengenes OTUs).

Maximum value of {MAPMATV4x,j} is computed.

The sequence 's' is classified to the Greengenes OTU 'y' (GGy), wherein, MAPMATV4x,y=max{MAPMATV4x,j}

The process is repeated for all query sequences and subsequently an OTU abundance table (TGG), in terms of Greengenes OTU IDs, is generated by cumulating the total number of sequenced reads from the given metagenomic sample that could be classified/attributed to each of the Greengenes OTUs.

In the second method, to represent the microbial community structure pertaining to a given metagenomic sample in an abundance table wherein the abundance of each microbe (OTU) is represented in terms percentage normalized values, the following steps are followed:

For a set of query sequences corresponding to a metagenomic sample, the abundance table/profile TOTUX is generated wherein the total number sequences assigned to each of the OTUXV4 OTUs are represented.

$$T_{OTUX} = \begin{pmatrix} a \\ b \\ C \\ \vdots \\ Z \end{pmatrix} \ldots \ldots OTUX_{v4}1, OTUX_{v4}2, OTUX_{v4}3, \ldots OTUX_{v}i$$

For example, TOTUX can be represented in form of a column matrix (of size NOTUX×1) as depicted above wherein T varies from 1 to NOTUX, i.e. the total number of OTUXV4 OTUs, and wherein 'a' is the number of sequences assigned to the OTU OTUXV41, 'b' is the number of sequences assigned to OTUXV42, 'c' is the number of sequences assigned to OTUXV43, and so on.

Obtain an OTU abundance table/profile (TGGraw) for the set of query sequences, in terms of Greeengenes OTU IDs by multiplying the matrix MAPMATV4 with the matrix TOTUX. It may be noted that given the nature of the MAPMAT matrix, the abundance values for each of the Greengenes OTUs in TGGraw may be a fractional value.

$$T_{GGraw} = MAPMATv4 * T_{OTUX}$$

Wherein, TGGraw is a column matrix of size (NGG×1), and NGG is the total number of Greengenes OTUs.

Obtain a percentage normalized OTU abundance table/profile (TGG %) by performing the following transformation on each element of TGGraw $$TGG\ \%\ j = \frac{TGGraw\ j}{\sum_{j=1}^{NGG} TGGraw\ j} * 100$$

Wherein, TGG % is a column matrix of size (NGG×1), and NGG is the total number of Greengenes OTUs.

In the last step, the abundance of taxonomic groups present in the metagenomic sample, as obtained in the form of either of the three column matrices, viz. $T_{OTUX}$, $T_{GG}$ and $T_{GG\ \%}$, are further represented at any desired taxonomic level utilizing the taxonomic hierarchy information associated with the Greengenes OTUs. Thus, the accurate annotations/categorizations allow to effectively identify, in a metagenomic sample, the presence of specific taxonomic groups. The specific taxonomic groups can further be analyzed, which may include infectious microbial strains, industrially important microbes, etc. The accurate categorization further provides a framework for easy cross comparison of microbiome community structures sampled across different disconnected metagenomic studies.

In operation, a flowchart 200 illustrating the steps involved for identification and classification of operational taxonomic units (OTUs) in a metagenomic sample using short read amplicon sequences is shown in FIG. 3 according to an embodiment of the disclosure. Initially at step 202, the metagenomic sample is collected using the metagenomic sample collection module 124. The metagenomic sample can be collected from gut, skin, sea, soil etc. At next step 204, the collected metagenomic sample is then sequenced using the sequencer 126. In the next step 206, one of a conventional operational taxonomic unit (OTU) database 104 and a conventional reference sequence database 106 are obtained. The conventional OTU database 104 having a plurality of predefined segments of nucleotide sequences clustered into one or more of conventional operational taxonomic units (OTUs) and conventional taxonomic clades.

At step 208, a customized OTU database (OTUX) is created using a predefined segments of nucleotide sequences from one of the conventional OTU database or the conventional reference sequence database. The predefined segments of nucleotide sequences are clustered into customized OTUs using a sequence clustering technique. Further at step 210, the propensity of a customized OTU from the customized OTU database (OTUX) is calculated using a predefined formula. The propensity refers to a probability of the customized OTU being associated with one or more conventional taxonomic clades in the conventional reference sequence database 106, or the one or more conventional OTUs in the conventional OTU database 104

At the next step 212, a mapping matrix is created. The mapping matrix lists all values of propensities for each of the customized OTUs with respect to one or more conventional taxonomic clades and conventional OTUs. At step 214, the customized OTU database (OTUX) is utilized as a reference database for open reference OTU picking to classify the short read amplicon sequences (query sequences) corresponding to predefined segments in to appropriate customized OTUs. And finally at step 216, an abundance table is built depicting the proportion of the short read amplicon sequences classified into each of the customized OTUs, wherein the abundance table representing enhanced accuracy of classification of operational taxonomic units (OTUs) in the metagenomic sample.

According to an embodiment of the disclosure, the system 100 can also be validated as follows: For validating the utility of the presented innovation, the preprocessed MAPMAT is utilized for V4 region of the 16S rRNA gene, which was created using the above described procedure. To obtain sets of short metagenomic reads to be classified in to OTUs/other taxonomic groups using the presented method, multiple simulated metagenomes were created pertaining to four different environments, viz. gut of healthy children (GUT), healthy human skin (SKIN), Mediterranean sea (SEA), and soil (SOIL) using the following procedure. Publicly available datasets pertaining to metagenomic samples from the mentioned environments were retrieved. Overall proportions of different genera present in each of the environments were obtained. Subsequently, a simulated metagenome pertaining to a particular environment was created by randomly drawing full length 16S rRNA genes from the RDP database (v10.3), wherein the proportions of different genera in the randomly drawn subset of sequences fairly reflected the proportions observed in the considered publicly available datasets. 100 simulated metagenomic datasets (each constituting 10000 sequences) were created for each of the 4 environments ($D_{GUT/F}$, $D_{SKIN/F}$, $D_{SEA/F}$, $D_{SOIL/F}$). To mimic metagenomic datasets obtained through short read sequencing, only the V4 regions from each of the full-length sequences constituting these simulated metagenomes were cropped out and a corresponding set of simulated 'short-read' metagenomes ($D_{GUT/V4}$, $D_{SKIN/V4}$, $D_{SEA/V4}$, $D_{SOIL/V4}$) containing only the V4 regions were constructed.

Initially, the full length sequences belonging to each of the simulated metagenomic datasets ($D_{GUT/F}$, $D_{SKIN/F}$, $D_{SEA/F}$, $D_{SOIL/F}$) were subjected to 'OTU picking' (taxonomic classification at the OTU level) against the Greengenes database using the naïve Bayesian classifier as used by RDP (Wang's algorithm with a bootstrap confidence threshold of 80%). Given that full-length 16S rRNA gene sequences were compared against a full-length 16S rRNA sequence database, the results obtained reflected the best achievable OTU-classification using 16S rRNA amplicon sequencing (using the same algorithm) and was considered as the 'baseline' or the 'gold standard' (GS). The simulated 'short-read' metagenomic datasets were subsequently subjected to taxonomic classification using the following 2 methods:

(a) Conventional approach (CA): Each of the metagenomes belonging to the sets $D_{GUT/V4}$, $D_{SKIN/V4}$, $D_{SEA/V4}$, and $D_{SOIL/V4}$ were classified using the naïve Bayesian classifier as used by RDP (Wang's algorithm with a bootstrap confidence threshold of 80%), and with the Greengenes OTU database as a reference. These results represent the taxonomic classification that can be obtained using the conventional approach of OTU picking/taxonomic classification wherein short-read sequences (covering a certain region of a marker gene) is used as a query against a OTU database constituted of full length marker genes. For ease of comparison, abundance tables representing the proportion of OTUs (and other taxa), both in terms of raw sequence counts as well as percentage normalized abundance, were generated.

(b) OTUX approach (OTUX): Each of the metagenomes belonging to the sets $D_{GUT/V4}$, $D_{SKIN/V4}$, $D_{SEA/V4}$, and $D_{SOIL/V4}$ were classified using the naïve Bayesian classifier as used by RDP (Wang's algorithm with a bootstrap confidence threshold of 80%), and with the $OTUX_{V4}$ database as a reference. These results represent the taxonomic classification that can be obtained using the novel OTUX approach of OTU picking/taxonomic classification wherein short-read sequences (covering a certain region of a marker gene) is used as a query against a pre-computed OTU database corresponding to a specific hyper-variable region (V4 in this case). It may be noted that the obtained OTU abundance table ($T_{OTUX}$) reports the results in terms of $OTUX_{V4}$ OTU IDs and the results can be deemed to be equivalent to results obtained through 'de novo OTU-picking'. For ease of comparison, these results are mapped back in terms of Greengenes OTU IDs and provided in the OTU abundance table $T_{GG}$, wherein raw counts of sequences assigned to individual Greengenes OTUs are depicted. Furthermore, percentage normalized abundance table(s) $T_{GG\ \%}$ is also generated, wherein abundance/proportion of OTUs (and/or other taxa) are represented in percent normalized terms.

The results of both approaches, conventional (CA) and OTUX, obtained with the simulated 'short read' metagenomes, were compared based on the three parameters: (1) Accuracy of taxonomic assignments at OTU, Genus and Family level(s) assessed in terms of correct number of assignments (as per the GS/baseline) by conventional approach (CA) as well as OTUX approach; (2) Unifrac and Bray-Curtis distance between the GS/baseline percentage normalized abundance table and those generated by conventional (CA) and OTUX approaches; And (3) Computational Time and Memory utilized by the conventional (CA) and OTUX approaches.

The first and second parameters as mentioned above can be explained with following results. The following tables depict the improved performance of OTUX based OTU assignment proposed in this innovation as compared to conventional approaches. 100 simulated metagenomes for each of the 4 selected environments viz. gut, skin, sea, and soil were created. Each of the metagenomes constituted 10000 sequences encompassing the V4 variable region. The datasets were subjected to OTU assignment using the conventional approach (CA), i.e. using V region amplicons as query against Greengenes reference database as well as the OTUX approach (OTUX), i.e. using V region amplicons as query against OTUX reference databases corresponding to an appropriate V region. The OTUX assignments obtained for the individual sequences as well as the abundance table obtained with the OTUX approach ($T_{OTUX}$) was mapped back in terms of Greengenes OTU IDs ($T_{GG}$) for comparing the results of the two approaches. These taxonomic assignment results were assessed for correctness by comparing against a baseline/'Gold-Standard' (GS) which refers to the OTU assignments obtained using corresponding full-length 16S rRNA gene sequences against the Greengenes database.

Average number of correct assignments for 100 simulated metagenomes pertaining to each of the environments are depicted. A T-test has been performed to assess whether the results using OTUX significantly outperforms CA method. Additionally, percent normalized taxonomic abundance tables obtained by CA and OTUX has been compared against the GS (Gold-Standard) using Unifrac distances (both weighted and unweighted), and Bray-Curtis distances. The results indicate the superior performance of the OTUX method over CA method. Results obtained with different conventionally targeted V-regions (or combinations thereof) are provided as follows. The results have been depicted for different taxonomic levels, viz., OTU, genus and family.

(i) For OTU Level

| Averaged for 100 simulated metagenomes (each having 10000 sequences) | Environments | | | |
|---|---|---|---|---|
| | GUT | SKIN | SEA | SOIL |
| V4 Region | | | | |
| Correct predictions by OTUX | 5803.21 | 3796.71 | 4941.84 | 4156.57 |
| Correct predictions by CA | 2318.88 | 320.92 | 2182.47 | 2287.78 |
| T-test score | 647.99 | 721.05 | 641.73 | 435.75 |
| P-value | 0.00E+00 | 2.24E−234 | 7.85E−275 | 8.78E−271 |
| Unweighted Unifrac dist (GS vs OTUX) | 0.369 | 0.471 | 0.446 | 0.462 |
| Unweighted Unifrac dist (GS vs CA) | 0.503 | 0.647 | 0.601 | 0.628 |
| Weighted Unifrac dist (GS vs OTUX) | 0.289 | 0.235 | 0.242 | 0.225 |
| Weighted Unifrac dist (GS vs CA) | 0.331 | 0.466 | 0.406 | 0.337 |
| Bray Curtis dissimilarity (GS vs OTUX) | 0.471 | 0.375 | 0.357 | 0.333 |
| Bray Curtis dissimilarity (GS vs CA) | 0.577 | 0.676 | 0.570 | 0.464 |
| V2V3 Region | | | | |
| Correct predictions by OTUX | 5448.5 | 5371.45 | 6357.35 | 5547.01 |
| Correct predictions by CA | 3808.17 | 1800.91 | 3183.1 | 4706.66 |
| T-test score | 281.45 | 623.68 | 688.47 | 159.73 |
| P-value | 2.04E−258 | 1.75E−306 | 4.04E−290 | 1.21E−210 |
| Unweighted Unifrac dist (GS vs OTUX) | 0.302 | 0.324 | 0.330 | 0.329 |
| Unweighted Unifrac dist (GS vs CA) | 0.311 | 0.356 | 0.370 | 0.300 |
| Weighted Unifrac dist (GS vs OTUX) | 0.237 | 0.101 | 0.127 | 0.077 |
| Weighted Unifrac dist (GS vs CA) | 0.281 | 0.349 | 0.335 | 0.152 |
| Bray Curtis dissimilarity (GS vs OTUX) | 0.378 | 0.221 | 0.202 | 0.161 |
| Bray Curtis dissimilarity (GS vs CA) | 0.428 | 0.528 | 0.469 | 0.215 |
| V3V4 Region | | | | |
| Correct predictions by OTUX | 6262.35 | 5437.89 | 6296.22 | 4626.71 |
| Correct predictions by CA | 3077.94 | 1477.09 | 3292.01 | 4548.06 |
| T-test score | 470.76 | 718.45 | 602.28 | 15.97 |
| P-value | 1.84E−295 | 0.00E+00 | 6.89E−291 | 2.16E−37 |
| Unweighted Unifrac dist (GS vs OTUX) | 0.323 | 0.363 | 0.367 | 0.392 |
| Unweighted Unifrac dist (GS vs CA) | 0.382 | 0.406 | 0.377 | 0.369 |
| Weighted Unifrac dist (GS vs OTUX) | 0.241 | 0.124 | 0.128 | 0.141 |
| Weighted Unifrac dist (GS vs CA) | 0.315 | 0.348 | 0.324 | 0.149 |

| Averaged for 100 simulated metagenomes | Environments | | | |
|---|---|---|---|---|
| (each having 10000 sequences) | GUT | SKIN | SEA | SOIL |
| Bray Curtis dissimilarity (GS vs OTUX) | 0.412 | 0.264 | 0.200 | 0.262 |
| Bray Curtis dissimilarity (GS vs CA) | 0.501 | 0.560 | 0.458 | 0.230 |
| V5V6 Region | | | | |
| Correct predictions by OTUX | 5856.33 | 5471.54 | 6255.22 | 5226.09 |
| Correct predictions by CA | 3079.6 | 1492.12 | 2871.11 | 3710.12 |
| T-test score | 418.18 | 744.17 | 645.27 | 325.53 |
| P-value | 8.47E−287 | 0.00E+00 | 2.60E−303 | 1.77E−259 |
| Unweighted Unifrac dist (GS vs OTUX) | 0.338 | 0.359 | 0.368 | 0.410 |
| Unweighted Unifrac dist (GS vs CA) | 0.386 | 0.431 | 0.430 | 0.472 |
| Weighted Unifrac dist (GS vs OTUX) | 0.235 | 0.104 | 0.153 | 0.162 |
| Weighted Unifrac dist (GS vs CA) | 0.310 | 0.331 | 0.346 | 0.194 |
| Bray Curtis dissimilarity (GS vs OTUX) | 0.398 | 0.245 | 0.269 | 0.286 |
| Bray Curtis dissimilarity (GS vs CA) | 0.501 | 0.558 | 0.500 | 0.317 |

(ii) For Genus Level

| Averaged for 100 simulated metagenomes | Environments | | | |
|---|---|---|---|---|
| (each having 10000 sequences) | GUT | SKIN | SEA | SOIL |
| V4 Region | | | | |
| Correct predictions by OTUX | 8555.4 | 8882.65 | 6999.15 | 7910.04 |
| Correct predictions by CA | 7690.71 | 6453.09 | 6729.89 | 7019.75 |
| T-test score | 229.95 | 579.01 | 84.31 | 245.69 |
| P-value | 2.46E−232 | 0.00E+00 | 1.75E−155 | 1.96E−235 |
| Unweighted Unifrac dist (GS vs OTUX) | 0.089 | 0.226 | 0.151 | 0.109 |
| Unweighted Unifrac dist (GS vs CA) | 0.077 | 0.172 | 0.155 | 0.128 |
| Weighted Unifrac dist (GS vs OTUX) | 0.059 | 0.060 | 0.105 | 0.070 |
| Weighted Unifrac dist (GS vs CA) | 0.107 | 0.246 | 0.123 | 0.128 |
| Bray Curtis dissimilarity (GS vs OTUX) | 0.099 | 0.118 | 0.148 | 0.093 |
| Bray Curtis dissimilarity (GS vs CA) | 0.140 | 0.312 | 0.158 | 0.171 |
| V2V3 Region | | | | |
| Correct predictions by OTUX | 8572.26 | 9324.14 | 7766.74 | 8264.82 |
| Correct predictions by CA | 8635.28 | 9092.03 | 6579.84 | 6760.23 |
| T-test score | −15.15 | 80.60 | 284.14 | 376.72 |
| P-value | 6.31E−35 | 2.60E−152 | 1.65E−260 | 4.81E−265 |
| Unweighted Unifrac dist (GS vs OTUX) | 0.078 | 0.105 | 0.096 | 0.069 |
| Unweighted Unifrac dist (GS vs CA) | 0.046 | 0.053 | 0.045 | 0.070 |
| Weighted Unifrac dist (GS vs OTUX) | 0.053 | 0.031 | 0.072 | 0.059 |
| Weighted Unifrac dist (GS vs CA) | 0.035 | 0.037 | 0.133 | 0.159 |
| Bray Curtis dissimilarity (GS vs OTUX) | 0.092 | 0.077 | 0.107 | 0.088 |
| Bray Curtis dissimilarity (GS vs CA) | 0.045 | 0.049 | 0.177 | 0.204 |
| V3V4 Region | | | | |
| Correct predictions by OTUX | 8053.54 | 9371.94 | 8011.17 | 7946.09 |
| Correct predictions by CA | 8401.74 | 8353.05 | 7123.73 | 8309.01 |
| T-test score | −77.00 | 292.51 | 222.56 | −90.05 |
| P-Value | 1.51E−145 | 2.03E−238 | 5.23E−236 | 4.50E−158 |
| Unweighted Unifrac dist (GS vs OTUX) | 0.043 | 0.106 | 0.096 | 0.066 |
| Unweighted Unifrac dist (GS vs CA) | 0.057 | 0.055 | 0.041 | 0.055 |
| Weighted Unifrac dist (GS vs OTUX) | 0.087 | 0.027 | 0.053 | 0.067 |
| Weighted Unifrac dist (GS vs CA) | 0.052 | 0.094 | 0.094 | 0.031 |
| Bray Curtis dissimilarity (GS vs OTUX) | 0.123 | 0.069 | 0.083 | 0.095 |
| Bray Curtis dissimilarity (GS vs CA) | 0.069 | 0.123 | 0.123 | 0.042 |
| V5V6 Region | | | | |
| Correct predictions by OTUX | 8799.65 | 9243.32 | 7503.73 | 7103.06 |
| Correct predictions by CA | 8109.87 | 8178.85 | 5482.86 | 7507.01 |
| T-test score | 194.77 | 285.25 | 445.08 | −86.34 |
| P-value | 1.18E−227 | 6.34E−257 | 1.30E−292 | 1.61E−158 |
| Unweighted Unifrac dist (GS vs OTUX) | 0.151 | 0.180 | 0.154 | 0.110 |
| Unweighted Unifrac dist (GS vs CA) | 0.048 | 0.068 | 0.066 | 0.049 |
| Weighted Unifrac dist (GS vs OTUX) | 0.042 | 0.035 | 0.095 | 0.156 |
| Weighted Unifrac dist (GS vs CA) | 0.076 | 0.106 | 0.209 | 0.094 |
| Bray Curtis dissimilarity (GS vs OTUX) | 0.082 | 0.079 | 0.134 | 0.214 |
| Bray Curtis dissimilarity (GS vs CA) | 0.098 | 0.138 | 0.271 | 0.123 |

(iii) For Family Level

| Averaged for 100 simulated metagenomes (each having 10000 sequences) | Environments | | | |
|---|---|---|---|---|
| | GUT | SKIN | SEA | SOIL |
| V4 Region | | | | |
| Correct predictions by OTUX | 9921.11 | 9697.28 | 9330.66 | 9299.72 |
| Correct predictions by CA | 9798.95 | 8697.26 | 9333.41 | 9128.97 |
| T-test score | 84.68 | 414.59 | −1.55 | 82.57 |
| P-value | 3.05E−141 | 4.83E−291 | 1.22E−01 | 1.28E−145 |
| Unweighted Unifrac dist (GS vs OTUX) | 0.088 | 0.071 | 0.070 | 0.023 |
| Unweighted Unifrac dist (GS vs CA) | 0.026 | 0.013 | 0.029 | 0.026 |
| Weighted Unifrac dist (GS vs OTUX) | 0.013 | 0.028 | 0.027 | 0.015 |
| Weighted Unifrac dist (GS vs CA) | 0.010 | 0.097 | 0.017 | 0.020 |
| Bray Curtis dissimilarity (GS vs OTUX) | 0.046 | 0.076 | 0.060 | 0.023 |
| Bray Curtis dissimilarity (GS vs CA) | 0.013 | 0.126 | 0.022 | 0.027 |
| V2V3 Region | | | | |
| Correct predictions by OTUX | 9801.26 | 9822.84 | 9499.73 | 9333.05 |
| Correct predictions by CA | 9721.21 | 9689.8 | 9462.58 | 9312.76 |
| T-test score | 39.77 | 69.30 | 25.08 | 10.78 |
| P-value | 5.04E−95 | 1.95E−135 | 5.03E−62 | 1.28E−21 |
| Unweighted Unifrac dist (GS vs OTUX) | 0.035 | 0.067 | 0.061 | 0.049 |
| Unweighted Unifrac dist (GS vs CA) | 0.009 | 0.026 | 0.010 | 0.018 |
| Weighted Unifrac dist (GS vs OTUX) | 0.023 | 0.022 | 0.025 | 0.026 |
| Weighted Unifrac dist (GS vs CA) | 0.018 | 0.020 | 0.007 | 0.006 |
| Bray Curtis dissimilarity (GS vs OTUX) | 0.066 | 0.068 | 0.055 | 0.036 |
| Bray Curtis dissimilarity (GS vs CA) | 0.023 | 0.028 | 0.009 | 0.008 |
| V3V4 Region | | | | |
| Correct predictions by OTUX | 9932.18 | 9926.97 | 9535.05 | 9383.12 |
| Correct predictions by CA | 9848.85 | 9846.84 | 9525.05 | 9382.02 |
| T-test score | 66.98 | 60.62 | 8.76 | 0.80 |
| P-value | 2.07E−122 | 1.47E−118 | 8.93E−16 | 4.25E−01 |
| Unweighted Unifrac dist (GS vs OTUX) | 0.024 | 0.023 | 0.014 | 0.012 |
| Unweighted Unifrac dist (GS vs CA) | 0.001 | 0.003 | 0.005 | 0.012 |
| Weighted Unifrac dist (GS vs OTUX) | 0.016 | 0.011 | 0.012 | 0.012 |
| Weighted Unifrac dist (GS vs CA) | 0.008 | 0.009 | 0.002 | 0.001 |
| Bray Curtis dissimilarity (GS vs OTUX) | 0.047 | 0.047 | 0.029 | 0.019 |
| Bray Curtis dissimilarity (GS vs CA) | 0.011 | 0.012 | 0.003 | 0.001 |
| V5V6 Region | | | | |
| Correct predictions by OTUX | 9948.13 | 9834.1 | 9532.83 | 9316.6 |
| Correct predictions by CA | 9401.43 | 9702.02 | 9483.68 | 9372.81 |
| T-test score | 228.65 | 69.12 | 34.35 | −38.16 |
| P-value | 8.47E−157 | 2.40E−133 | 4.98E−82 | 4.02E−92 |
| Unweighted Unifrac dist (GS vs OTUX) | 0.109 | 0.115 | 0.081 | 0.065 |
| Unweighted Unifrac dist (GS vs CA) | 0.018 | 0.003 | 0.003 | 0.003 |
| Weighted Unifrac dist (GS vs OTUX) | 0.017 | 0.019 | 0.020 | 0.029 |
| Weighted Unifrac dist (GS vs CA) | 0.042 | 0.019 | 0.005 | 0.001 |
| Bray Curtis dissimilarity (GS vs OTUX) | 0.066 | 0.061 | 0.045 | 0.041 |
| Bray Curtis dissimilarity (GS vs CA) | 0.055 | 0.025 | 0.007 | 0.002 |

The third parameter of 'computation time and memory utilized' as mentioned above can be explained with following results. Table below depicting the average computational time required by the conventional (CA) and OTUX approaches for classifying each sequence. Peak memory usage by these approaches has also been indicated. The validation test was performed on an Intel Xeon based server with 40 processing cores (2.0 GHz) and a total RAM of 128 GB. The time and memory usage values indicated in the table has been normalized for a single processing core.

| Targeted V-Region | Average time (in seconds) required for classifying a single read | |
|---|---|---|
| | OTUX approach | CA |
| V1 | 0.217 | 0.507 |
| V2 | 0.854 | 1.703 |
| V3 | 0.640 | 1.156 |

-continued

| Targeted V-Region | Average time (in seconds) required for classifying a single read | |
|---|---|---|
| | OTUX approach | CA |
| V4 | 1.064 | 2.078 |
| V5 | 0.427 | 1.003 |
| V6 | 0.482 | 1.248 |
| V7 | 0.552 | 1.206 |
| V8 | 0.779 | 1.568 |
| V9 | 0.202 | 1.031 |
| V1V2 | 3.214 | 5.135 |
| V1V3 | 7.265 | 12.857 |
| V2V3 | 5.308 | 9.225 |
| V3V4 | 3.681 | 7.035 |
| V3V5 | 7.951 | 14.235 |
| V3V6 | 12.794 | 19.902 |
| V4V5 | 4.616 | 8.417 |
| V4V6 | 8.007 | 14.345 |
| V5V6 | 3.723 | 6.501 |

-continued

| Targeted V-Region | Average time (in seconds) required for classifying a single read | |
|---|---|---|
| | OTUX approach | CA |
| V6V8 | 4.711 | 9.281 |
| Peak memory Usage | 1.078 GB | 1.261 GB |

The results indicated superior performance of the OTUX method over the conventional approach in every aspect compared. Furthermore, the mapping back feature implemented in the OTUX method allows a realistic cross comparison between metagenomic results generated with short-read sequencing targeting any of the hyper-variable regions.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for identification and classification of operational taxonomic units (OTUs) of one or more microbes in a metagenomic sample using short read amplicon sequences and ascertain at least one microbial community structure pertaining to the one or more microbes from the metagenomic sample, the method comprising:

receiving the metagenomic sample collected from gut, skin, sea or soil;

sequencing the metagenomic sample, using a sequencer (126);

accessing, by a processor (110), at least one of a conventional operational taxonomic unit (OTU) database and a conventional reference sequence database, wherein the conventional OTU database has thousands of nucleotide sequences clustered into one or more of conventional operational taxonomic units (OTUs) and conventional taxonomic clades;

creating, by the processor (110), a customized OTU database (OTUX) using a plurality of predefined segments of nucleotide sequences from the conventional operational taxonomic unit (OTU) database or the conventional reference sequence database, wherein the customized OTU database (OTUX) comprises customized OTUs, wherein the predefined segments of nucleotide sequences are clustered into the customized OTUs using a sequence clustering technique, wherein the predefined segment of nucleotide sequences from the conventional OTU database or the conventional reference sequence database corresponds to a portion of a full length DNA sequence that is targeted through amplicon sequencing, and different nucleotide sequences correspond to different portions of the full length DNA sequence that is extracted or amplified using different primers, and wherein the step of creating the customized OTUs comprises:

retrieving all unaligned sequences from the conventional OTU database and the conventional reference sequence database;

extracting the predefined segment of a marker gene for each unaligned sequences present in the conventional OTU database, wherein the marker gene is the regions of nucleotide sequences obtained from the metagenomic sample;

clustering the extracted sequences based on a predefined similarity threshold into the customized OTUs using the sequence clustering technique; and compiling the clustered customized OTUs to constitute the customized OTU database;

calculating, by the processor (110), propensity of each customized OTU from the customized OTU database (OTUX) using a formula, wherein the propensity refers to a probability of a customized OTU being associated with one or more conventional taxonomic clades in the conventional reference sequence database and the conventional OTUs in the conventional OTU database, wherein the propensities are calculated using the formula:

(a number of the predefined segments of nucleotide sequences clustered into a customized OTU corresponding to the customized OTU database (OTUX) whose full-length counterparts are assigned to a conventional OTU or a conventional taxonomic clade present in the conventional OTU database)/(total number of predefined segments of nucleotide sequences clustered into the customized OTU corresponding to the customized OTU database(OTUX));

creating, by the processor (110), a mapping matrix listing all values of propensities for each of the customized OTUs with respect to one or more conventional taxonomic clades and conventional OTUs;

utilizing, supervised machine learning classification technique by the processor (110), on the customized OTU database (OTUX) as a reference database for open reference OTU picking to classify short read amplicon sequences obtained from the sequenced metagenomic sample corresponding to the predefined segments into appropriate customized OTUs, wherein classifying the short read amplicon sequences into the appropriate customized OTUs reduces average computational time and memory utilization relative to one or more conventional approaches for classifying sequences;

building, by the processor (110), an abundance table depicting the proportion of the short read amplicon sequences classified into each of the customized OTUs either by cumulating total number of sequenced reads from the metagenomic sample which is classified to the customized OTUs or by representing microbial community structure pertaining to the metagenomic sample, wherein abundance of each microbe OTU is represented in terms of percentage normalized abundance values, wherein the abundance table representing enhanced accuracy of classification of operational taxonomic units (OTUs) in the metagenomic sample;

mapping back, by the processor (110), the customized OTUs using the mapping matrix to represent proportion of the short read amplicon sequences classified into the customized OTUs in terms of the one or more of conventional OTUs and conventional taxonomic clades;

ascertain at least one microbial community structure pertaining to the metagenomic sample using the abundance table and the mapping matrix, and representing the abundance of taxonomic groups present in the abundance table in the form of a taxonomic level utilizing taxonomic hierarchy information associated with at least one of the customized OTUs and the mapped back conventional OTUs, the representation of the taxonomic groups in the form of taxonomic levels enables identification of presence of specific taxonomic groups pertaining to the one or more microbes based on the ascertained at least one microbial community structure which facilitates cross comparison of the classified short read amplicon sequences with the taxonomic analysis result from different disconnected metagenomic studies, wherein different sequencing technologies as well as different marker sequences or amplicons are used in the different disconnected metagenomic studies, wherein the taxonomic level includes OTU, genus and family level, and wherein the specific taxonomic groups are analyzed for infectious microbial strains, industrially important microbes.

2. The method of claim 1, wherein the conventional reference database is one of a Greengenes database, SILVA database or RDP database containing full length 16S rRNA gene sequences.

3. The method of claim 1, wherein the marker gene is prokaryotic 16S rRNA gene having nine regions V1 to V9.

4. The method of claim 1, wherein short read amplicon sequence is used as a query against the customized OTU database corresponding to a hyper-variable region, wherein the hyper-variable region is V4 region of 16S rRNA gene.

5. The method of claim 1, wherein the one or more microbes comprise infectious microbe or industrially useful microbe.

6. A system for identification and classification of operational taxonomic units (OTUs) of one or more microbes in a metagenomic sample using short read amplicon sequences and ascertain at least one microbial community structure pertaining to the one or more microbes from the metagenomic sample, the system comprises:

a sequencer (126) for receiving the metagenomic sample collected from gut, skin, sea or soil and sequencing the metagenomic sample;

a memory (108); and a processor (110) in communication with the memory (108), wherein the processor configured to perform the steps of:

accessing at least one of a conventional operational taxonomic unit (OTU) database and a conventional reference sequence database, wherein the conventional OTU database has thousands of nucleotide sequences clustered into one or more of conventional operational taxonomic units (OTUs) and conventional taxonomic clades;

creating a customized operational taxonomic unit (OTU) database (OTUX) using a plurality of predefined segments of nucleotide sequences from the conventional operational taxonomic unit (OTU) database or the conventional reference sequence database, wherein the conventional OTU database having a plurality of nucleotide sequences clustered into one or more of conventional operational taxonomic units (OTUs) and conventional taxonomic clades, wherein the customized OTU database (OTUX) comprises customized OTUs, wherein the predefined segments of nucleotide sequences are clustered into the customized OTUs using a sequence clustering technique, wherein the predefined segment of nucleotide sequences from the conventional OTU database or the conventional reference sequence database corresponds to a portion of a full length DNA sequence that is targeted through amplicon sequencing, and different nucleotide sequences correspond to different portions of the full length DNA sequence that is extracted or amplified using different primers, and wherein the step of creating the customized OTUs comprises:

retrieving all unaligned sequences from the conventional OTU database and the conventional reference sequence database;

extracting the predefined segment of a marker gene for each unaligned sequences present in the conventional OTU database, wherein the marker gene is the regions of nucleotide sequences obtained from the metagenomic sample;

clustering the extracted sequences based on a predefined similarity threshold into the customized OTUs using the sequence clustering technique; and compiling the clustered customized OTUs to constitute the customized OTU database;

calculating propensity of each customized OTU from the customized OTU database (OTUX) using a formula, wherein the propensity refers to a probability of a customized OTU being associated with one or more conventional taxonomic clades in the conventional reference sequence database and the conventional OTUs in the conventional OTU database, wherein the propensities are calculated using the formula:

(a number of the predefined segments of nucleotide sequences clustered into a customized OTU corresponding to the customized OTU database (OTUX) whose full-length counterparts are assigned to a conventional OTU or a conventional taxonomic clade present in a conventional OTU database)/(total number of predefined segments of nucleotide sequences clustered into the customized OTU corresponding to the customized OTU database(OTUX));

creating a mapping matrix listing all values of propensities for each of the customized OTUs with respect to one or more conventional taxonomic clades and conventional OTUs;

utilizing supervised machine learning classification technique on the customized OTU database (OTUX) as a reference database for open reference OTU picking to classify short read amplicon sequences obtained from the sequenced metagenomic sample corresponding to predefined segments into appropriate customized OTUs, wherein classifying the short read amplicon sequences into the appropriate customized OTUs reduces average computational time and memory utilization relative to one or more conventional approaches for classifying sequences;

building an abundance table depicting the proportion of the short read amplicon sequences classified into each of the customized OTUs either by cumulating total number of sequenced reads from the metagenomic sample which is classified to the customized OTUs or by representing microbial community structure pertaining to the metagenomic sample, wherein abundance of each microbe OTU is represented in terms of percentage normalized abundance values, wherein the abundance table representing enhanced accuracy of classification of operational taxonomic units (OTUs) in the metagenomic sample;

mapping back the customized OTUs using the mapping matrix to represent proportion of the short read amplicon sequences classified into the customized OTUs in terms of the one or more of conventional OTUs and conventional taxonomic clades;

ascertaining at least one microbial community structure pertaining to the metagenomic sample using the abundance table and the mapping matrix, and representing the abundance of taxonomic groups present in the abundance table in the form of a taxonomic level utilizing taxonomic hierarchy information associated with at least one of the customized OTUs and the mapped back conventional OTUs, the representation of the taxonomic groups in the form of taxonomic levels enables identification of presence of specific taxonomic groups pertaining to the one or more microbes based on the ascertained at least one microbial community structure which facilitates cross comparison of the classified short read amplicon sequences with the taxonomic analysis result from different disconnected metagenomic studies, wherein different sequencing technologies as well as different marker sequences or amplicons are used in the different disconnected metagenomic studies, wherein the taxonomic level includes OTU, genus and family level, and wherein the specific taxonomic groups are analyzed for infectious microbial strains, industrially important microbes.

7. A non-transitory computer-readable medium having embodied thereon a computer program executed by a processor for identification and classification of operational taxonomic units (OTUs) of one or more microbes in a metagenomic sample using short read amplicon sequences and ascertaining at least one microbial community structure pertaining to the one or more microbes from the metagenomic sample, the method comprising processor implemented steps of:

receiving the metagenomic sample collected from gut, skin, sea or soil;

sequencing the metagenomic sample using a sequencer (126);

accessing, by a processor (110), at least one of a conventional operational taxonomic unit (OTU) database and a conventional reference sequence database, wherein the conventional OTU database has thousands of nucleotide sequences clustered into one or more of conventional operational taxonomic units (OTUs) and conventional taxonomic clades;

creating, by the processor (110), a customized OTU database (OTUX) using a plurality of predefined segments of nucleotide sequences from the conventional OTU database or the conventional reference sequence database, wherein the customized OTU database (OTUX) comprises customized OTUs, wherein the predefined segments of nucleotide sequences are clustered into the customized OTUs using a sequence clustering technique, wherein the predefined segment of nucleotide sequences from the conventional OTU database or the conventional reference sequence database corresponds to a portion of a full length DNA sequence that is targeted through amplicon sequencing, and different nucleotide sequences correspond to different portions of the full length DNA sequence that is extracted or amplified using different primers, and wherein the step of creating the customized OTUs comprises:

retrieving all unaligned sequences from the conventional OTU database and the conventional reference sequence database;

extracting the predefined segment of a marker gene for each unaligned sequences present in the conventional OTU database, wherein the marker gene is the regions of nucleotide sequences obtained from the metagenomic sample;

clustering the extracted sequences based on a predefined similarity threshold into the customized OTUs using the sequence clustering technique; and compiling the clustered customized OTUs to constitute the customized OTU database;

calculating, by the processor (110), propensity of a customized OTU from the customized OTU database (OTUX) using a formula, wherein the propensity refers to a probability of a customized OTU being associated with one or more conventional taxonomic clades in the conventional reference sequence database and the conventional OTUs in the conventional OTU database, wherein the propensities are calculated using the formula:

(a number of the predefined segments of nucleotide sequences clustered into a customized OTU corresponding to the customized OTU database (OTUX) whose full-length counterparts are assigned to a conventional OTU or a conventional taxonomic clade present in a conventional OTU database)/(total number of predefined segments of nucleotide sequences clustered into the customized OTU corresponding to the customized OTU database(OTUX));

creating, by the processor (110), a mapping matrix listing all values of propensities for each of the customized OTUs with respect to one or more conventional taxonomic clades and conventional OTUs;

utilizing, supervised machine learning classification technique, by the processor (110), on the customized OTU database (OTUX) as a reference database for open reference OTU picking to classify short read amplicon sequences obtained from the sequenced metagenomic sample corresponding to predefined segments in to appropriate customized OTUs, wherein classifying the short read amplicon sequences into the appropriate customized OTUs reduces average computational time and memory utilization relative to one or more conventional approaches for classifying sequences; and building, by the processor (110), an abundance table depicting the proportion of the short read amplicon sequences classified into each of the customized OTUs either by cumulating total number of sequenced reads from the metagenomic sample which is classified to the customized OTUs or by representing microbial community structure pertaining to the metagenomic sample, wherein abundance of each microbe OTU is represented in terms of percentage normalized abundance values, wherein the abundance table representing enhanced accuracy of classification of operational taxonomic units (OTUs) in the metagenomic sample;

mapping back by the processor (110), the customized OTUs using the mapping matrix to represent proportion of the short read amplicon sequences classified into the customized OTUs in terms of the one or more of conventional OTUs and conventional taxonomic clades;

ascertaining at least one microbial community structure pertaining to the metagenomic sample using the abundance table and the mapping matrix, and representing the abundance of taxonomic groups present in the abundance table in the form of a taxonomic level utilizing taxonomic hierarchy information associated with at least one of the customized OTUs and the mapped back conventional OTUs, the representation of the taxonomic groups in the form of taxonomic levels enables identification of presence of specific taxonomic groups pertaining to the one or more microbes based on the ascertained at least one microbial community structure which facilitates cross comparison of the classified short read amplicon sequences with the taxonomic analysis result from different disconnected metagenomic studies, wherein different sequencing technologies as well as different marker sequences or amplicons are used in the different disconnected metagenomic studies, wherein the taxonomic level includes OTU, genus and family level, and wherein the specific taxonomic groups are analyzed for infectious microbial strains, industrially important microbes.

* * * * *